(12) United States Patent
Morano, III et al.

(10) Patent No.: US 12,339,074 B1
(45) Date of Patent: Jun. 24, 2025

(54) HEAT EXCHANGER TUBING ASSEMBLY AND CONDUCTIVE CASING

(71) Applicant: Carolina Components Group, Inc., Durham, NC (US)

(72) Inventors: Lawrence George Morano, III, Raleigh, NC (US); Mark Christopher McElligott, Windham, NH (US)

( * ) Notice: Subject to any disclaimer, the term of this patent is extended or adjusted under 35 U.S.C. 154(b) by 0 days.

(21) Appl. No.: 19/044,179

(22) Filed: Feb. 3, 2025

Related U.S. Application Data (63) Continuation of application No. PCT/US2024/024632, filed on Apr. 15, 2024.

(51) Int. Cl.
 *F28F 9/26* (2006.01)
 *F28F 3/12* (2006.01)

(52) U.S. Cl.
 CPC ............... *F28F 3/12* (2013.01); *F28F 9/26* (2013.01); *F28F 2255/00* (2013.01); *F28F 2275/122* (2013.01)

(58) Field of Classification Search
 CPC .... F28F 3/12; F28F 9/26; F24D 3/125; F24D 3/142
 See application file for complete search history.

(56) References Cited

U.S. PATENT DOCUMENTS 4,583,583 A * 4/1986 Wittel ............... H01M 8/04074
 165/170
5,899,077 A * 5/1999 Wright .................. H10N 10/00
 62/3.7

(Continued)

FOREIGN PATENT DOCUMENTS

CN 214666309 U 11/2021
CN 214892742 U 11/2021
(Continued)

OTHER PUBLICATIONS

Park, Tae Wook, PCT Written Opinion of the International Searching Authority for International Application No. PCT/US2024/024632, Dec. 24, 2024, 6 pages, Korean Intellectual Property Office, Daejeon, South Korea.
(Continued)

*Primary Examiner* — Eric S Ruppert
(74) *Attorney, Agent, or Firm* — Kevin E Flynn; FLYNN IP LAW (57) ABSTRACT

A heat exchanger tubing assembly for insertion into a channel in a conductive casing, so that thermal treatment applied to the conductive casing may be transferred through the heat exchanger tubing assembly to a liquid passing through the heat exchanger tubing assembly. The heat exchanger tubing assembly having two conductive segment having and elevated thermal conductivity value and being short enough to fit within the conductive casing. The conductive segments having barbed end portions and a flange that extends radially outward from the conductive segment. The flanges engage with flange receiving voids in the conductive casing to help position the heat exchanger tubing assembly within the conductive casing. The conductive casing having compression rings to press down on portions of flexible tubing that engages with the conductive segments to form enhanced barbed connections. The flexible tubing having lower thermal conductivity than the conductive segments.

19 Claims, 11 Drawing Sheets

(56) References Cited

U.S. PATENT DOCUMENTS

| | | |
|---|---|---|
| 9,528,083 B2 | 12/2016 | Staheli |
| 2007/0199190 A1 | 8/2007 | Karoliussen |
| 2023/0258290 A1 | 8/2023 | Nowicki |

FOREIGN PATENT DOCUMENTS

| | | | |
|---|---|---|---|
| KR | 20130040987 A | * | 4/2013 |
| KR | 1020130012809 A | | 2/2023 |

OTHER PUBLICATIONS

Polymers with High Thermal Conductivity, NanoEngineering: Research, available at https://web.mit.edu/nanoengineering/research/polymers.shtml# on Apr. 3, 2024, 2 pages, Massachusetts Institute of Technology, Cambridge, Massachusetts, United States of America.

Nylon, available at https://en.wikipedia.org/wiki/Nylon on Apr. 3, 2024, 16 pages, Wikimedia Foundation, San Francisco, California, United States of America.

* cited by examiner

| 1004 | Open the conductive casing and remove any previously used heat exchanger tubing assembly to leave an empty channel. |

| 1008 | Place the new heat exchanger tubing assembly into the channel including placement of the flanges into the flange retention voids. |

| 1012 | Close the conductive casing and reversibly attach the first piece to the second piece which presses compression rings into tubing above non-raised gaps of the barbed portions of the conductive segments to enhance the barbed connections. |

HEAT EXCHANGER TUBING ASSEMBLY AND CONDUCTIVE CASING

BACKGROUND

Field of the Disclosure

This disclosure relates generally to heat exchangers for altering the temperature of a liquid passing through tubing. These heat exchangers may be used in a variety of industries including biopharmaceutical production.

Vocabulary

A, An.

In this application, and the claims that follow, the terms a, an, or the identification of a single thing should be read as at least one unless such an interpretation is impossible within the context of the entirety of the specification. For example, the use of the terms sole, only, or the phrase not more than one would indicate that a single item is intended.

Gne and Gnes.

To avoid the awkward he/she and his/her or the potentially confusing singular use of they and their, this application uses the Gender-Neutral Expression—gne, the possessive pronoun—gnes, reflexive pronoun—gneself and the object form—gnerm. Thus—gne looked for gnes notebook gneself as gnes friends would not help gnerm Or.

Unless explicit to the contrary, the word "or" should be interpreted as an inclusive or rather than an exclusive or. Thus, the default meaning of or should be the same as the more awkward and/or.

Proximal and Distal.

Proximal and distal are useful ways to referencing an item that has two ends. For this application, proximal is towards the beginning of the flow path for the liquid and distal is towards the end of the flow path.

Set.

Unless explicit to the contrary, the word "set" should be interpreted as a group of one or more items.

Step.

The term step may be used in descriptions within this disclosure. For purposes of clarity, one distinct act or step may be discussed before beginning the discussion of another distinct act or step. The term step should not be interpreted as implying any particular order among or between various steps disclosed unless the specific order of individual steps is expressly indicated.

Substantially.

Frequently, when describing an industrial process it is useful to note that a given parameter is substantially met. Examples may be substantially parallel, substantially perpendicular, substantially uniform, and substantially flat. In this context, substantially X means that for purposes of this industrial process it is X. So something that may not be absolutely parallel but is for all practical purposes parallel, is substantially parallel. Likewise, mixed air that has substantially uniform temperature would have temperature deviations that were inconsequential for that industrial process.

As recognized in C. E. Equipment Co. v. United States, 13 U.S.P.Q.2d 1363, 1368 (Cl. Ct. 1989), the word "substantially" in patent claims gives rise to some definitional leeway-thus the word "substantially" may prevent avoidance of infringement by minor changes that do not affect the results sought to be accomplished.

Units.

Note that in order to provide focus on specific functions, the description below will reference various "units". In this context, a unit implies the required resources to perform a given set of functions. This may include a combination of electro-mechanical devices such as a microphone or a camera and the processing power to control the devices then manipulate the data obtained by the devices. In some instances, the functionality from several individually discussed units may be performed using physical components that are shared by several of the units discussed below. Unless explicit to the contrary, the word "or" should be interpreted as an inclusive or rather than an exclusive or. Thus, the default meaning of or should be the same as the more awkward and/or.

SUMMARY OF THE DISCLOSURE

Aspects of the teachings contained within this disclosure are addressed in the claims submitted with this application upon filing. Rather than adding redundant restatements of all the contents of the claims, these claims should be considered incorporated by reference into this summary.

This summary is meant to provide an introduction to the concepts that are disclosed within the specification without being an exhaustive list of the many teachings and variations upon those teachings that are provided in the extended discussion within this disclosure. Thus, the contents of this summary should not be used to limit the scope of the claims that follow.

Inventive concepts are illustrated in a series of examples, some examples showing more than one inventive concept. Individual inventive concepts can be implemented without implementing all details provided in a particular example. It is not necessary to provide examples of every possible combination of the inventive concepts provide below as one of skill in the art will recognize that inventive concepts illustrated in various examples can be combined together in order to address a specific application.

Some aspects of the teachings of the present disclosure may be expressed as a heat exchanger tubing assembly for insertion into a channel in a conductive casing having a first piece and a second piece, so that thermal treatment applied to the conductive casing may be transferred through the heat exchanger tubing assembly to a liquid passing through the heat exchanger tubing assembly to create a heat-treated liquid. The heat exchanger tubing assembly having a set of at least two conductive segments, each conductive segment made of a first material of first thermal conductivity value, each conductive segment short enough to fit into the channel in the conductive casing so that neither a first end portion nor a second end portion of the conductive segment extends out of the conductive casing. Both the first end portion and the second end portion of each conductive segment having a barbed portion and a flange that extends radially outward from the conductive segment. Each conductive segment having a longitudinal bore to allow liquid to pass through the conductive segment.

The heat exchanger tubing assembly also having a first connector tube with a flexible tube connected to the first end portion of a first conductive segment to allow liquid to enter a proximal end of the first connector tube outside of the conductive casing and travel through a longitudinal channel then out a distal end of the first connector tube into the longitudinal bore of the first conductive segment. The flexible tube made of a second material with a second thermal conductivity value which is lower than the first thermal conductivity value.

The heat exchanger tubing assembly also having a first curved connector with an interior channel. The first curved connector made of a third material with a third thermal conductivity value which is lower than the first thermal conductivity value. The first curved connector connecting the second end portion of the first conductive segment and a first end portion of a second conductive segment;

The heat exchanger tubing assembly also having a second connector tube with flexible tube, connected to a distal end of a final conductive segment to allow liquid to enter a proximal end of the second connector tube inside of the conductive casing and travel out a distal end of the second connector tube outside of the conductive casing into a subsequent flow path for the heat-treated liquid. Wherein the set of flanges extending radially outward may be used to engage with flange receiving voids in the conductive casing to help position the heat exchanger tubing assembly within the conductive casing.

Aspects of the teachings of the present disclosure may be expressed as an enhanced barbed connection using at least one compression ring. The enhanced barbed connection having a barbed connection of a first tube with a flexible tube. The first tube having a flange that extends radially outward from the first tube near a distal end of the first tube. The distal end having a barbed section including at least a first raised portion and a second raised portion that each extends radially outward from the first tube and at least a first non-raised gap between at least the first raised portion and the second raised portion.

The flexible tube receives the barbed section in an interior bore for the flexible tube as the barbed section is advanced into the flexible tube until a leading edge of the flexible tube abuts a stop face of the first tube.

A first piece of a casing and a second piece of the casing that have:
 a channel that is sized to receive the barbed connection,
 a flange retention void for receipt of the flange;
 a first void that expands the channel radially outward around the first raised portion; and
 a second void that expands the channel radially outward around the second raised portion.

The first piece of the casing and the second piece of the casing forming a first compression ring between the first void and the second void as each piece has a compression ring segment that extends radially inward relative to the channel that receives the barbed connection so that when the first piece of the casing is drawn to the second piece of the casing. The at least one compression ring formed by the two compression ring segments pushes on the flexible tube between the first raised portion and the second raised portion to form the enhanced barbed connection.

Aspects of the teachings of the present disclosure may be expressed as an enhanced barbed connection using at least one compression ring. The enhanced barbed connection having a barbed connection of a first tube with a flexible tube. The first tube having a flange that extends radially outward from the first tube near a distal end of the first tube.

The distal end having a barbed section including at least a first raised portion that extends radially outward from the first tube and at least a first non-raised gap between the first raised portion and the flange. The flexible tube receives the barbed section in an interior bore for the flexible tube as the barbed section is advanced into the flexible tube until a leading edge the flexible tube abuts a stop face of the first tube.

The enhanced barbed connection involving a first piece of a casing and a second piece of the casing having a channel that is sized to receive the barbed connection. The first piece of the casing and the second piece of the casing each having a flange retention void for receipt of the flange. The first piece of casing and the second piece of casing having a first void that expands the channel radially outward around the first raised portion. The first piece of the casing and the second piece of the casing forming a first compression ring between the first void and the flange retention void as each piece has a compression ring segment that extends radially inward relative to the channel that receives the barbed connection. When the first piece of the casing is drawn to the second piece of the casing, the at least one compression ring formed by the two compression ring segments pushes on the flexible tube between the first void and the flange retention void to form the enhanced barbed connection.

Aspects of the teachings of the present disclosure may be expressed as a process to insert a new heat exchanger tubing assembly into a conductive casing. The process including opening the conductive casing and removing any previously used heat exchanger tubing assembly to empty a channel in the conductive casing.

The process including placing the new heat exchanger tubing assembly into the channel including placement of flanges into flange retention voids.

The process including closing the conductive casing and reversibly attach a first piece to a second piece which presses compression rings into flexible tubing above non-raised gaps of barbed portions of conductive segments to form a set of enhanced barbed connections.

Other systems, methods, features and advantages of the disclosed teachings will be immediately apparent or will become apparent to one with skill in the art upon examination of the following figures and detailed description. It is intended that all such additional systems, methods, features and advantages be included within the scope of and be protected by the accompanying claims.

BRIEF DESCRIPTION OF THE FIGURES

The disclosure can be better understood with reference to the following figures. The components in the figures are not necessarily to scale, emphasis instead being placed upon illustrating the principles of the disclosure. Moreover, in the figures, like reference numerals designate corresponding parts throughout the different views.

DETAILED DESCRIPTION

The presently disclosed subject matter is described with specificity to meet statutory requirements. However, the description itself is not intended to limit the scope of this patent. Rather, the inventors have contemplated that the claimed subject matter might also be embodied in other ways, to include different steps or elements similar to the ones described in this document, in conjunction with other present or future technologies. Moreover, although the term "step" may be used herein to connote different aspects of methods employed, the term should not be interpreted as implying any particular order among or between various steps herein disclosed unless and except when the order of individual steps is explicitly described.

Figure 1:
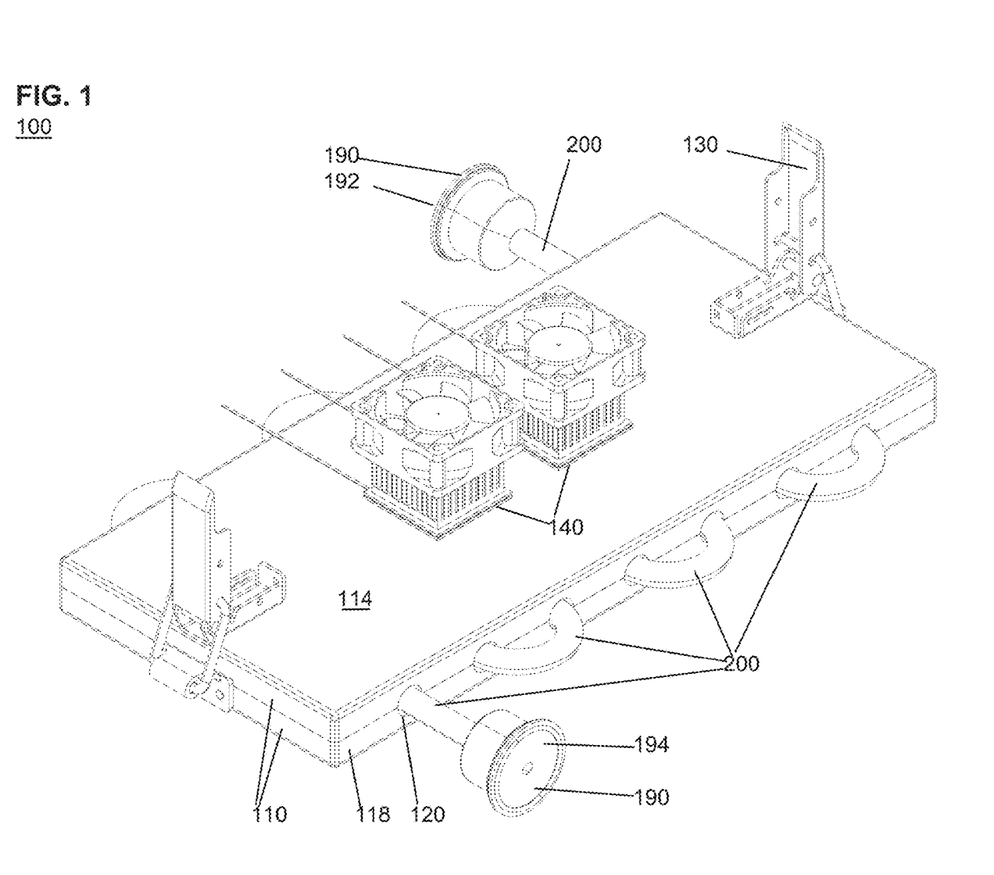
FIG. 1 shows a perspective view of a heat exchanger assembly 100.

FIG. 1

FIG. 1 shows a perspective view of a heat exchanger assembly 100. The heat exchanger assembly has a conductive casing 110 with a first piece 114 and a second piece 118. The first piece 114 may be moved relative to the second piece 118 so that a heat exchanger tubing assembly 200 may be placed into a channel 120 within the conductive casing 110. The first piece 114 may be held in close proximity to the second piece 118 through clasps 130 or other known attachment schemes including bolts that pass through the conductive casing, or threaded elements that pass through one of the two pieces into a threaded bore in the other piece. Many other reversible connection mechanisms such as cam locks are known to those of skill in the art.

The conductive casing 110 is made of a material with high thermal conductivity such as aluminum or another metal. The channel 120 in the conductive casing 110 requires manufacturing steps so that the conductive casing 110 is ideally not a single use item.

The heat exchanger tubing assembly 200 is typically a single use item so that a heat exchanger tubing assembly 200 may be used for a first process and then the heat exchanger assembly fitted with a new heat exchanger tubing assembly 200 may be used in a new process.

The heat exchanger tubing assembly 200 has a proximal end 192 which may have a fitting to allow connection to other tubing carrying the liquid to be heat treated before the heat treatment. The heat exchanger tubing assembly 200 has a distal end 224 which may have a fitting to allow connection to other tubing carrying the liquid after the heat treatment. The fittings shown here are sanitary fittings 190 inserted into tubing used in the medical, pharmaceutical, biopharmaceutical, food and beverage, or laboratory environments.

The heat exchanger assembly 100 passes heat treatment (heating or cooling) to alter the temperature of the liquid entering the proximal end 192 so that the liquid changes to have a temperature close to that of the conductive casing 110.

The way that the conductive casing 110 is heated or cooled is beyond the scope of this disclosure. One way of altering the temperature of the conductive casing is through the use of one or more Peltier devices 140. Peltier devices use the Peltier effect to provide thermoelectric cooling by using a solid-state heat pump. The Peltier device 140 could be used to apply either heat or cooling to the conductive casing 110. While only two Peltier devices 140 are shown here, one of skill in the art will appreciate that an array or matrix of Peltier devices 140 may be employed on just the one piece (114 or 118) of the conductive casing 110 or on both the first piece 114 and the second piece 118.

Alternatively, a conductive case a separate channel for a working fluid, could use the working fluid to alter the temperature of the conductive casing instead of using the Peltier device 140.

Figure 2:
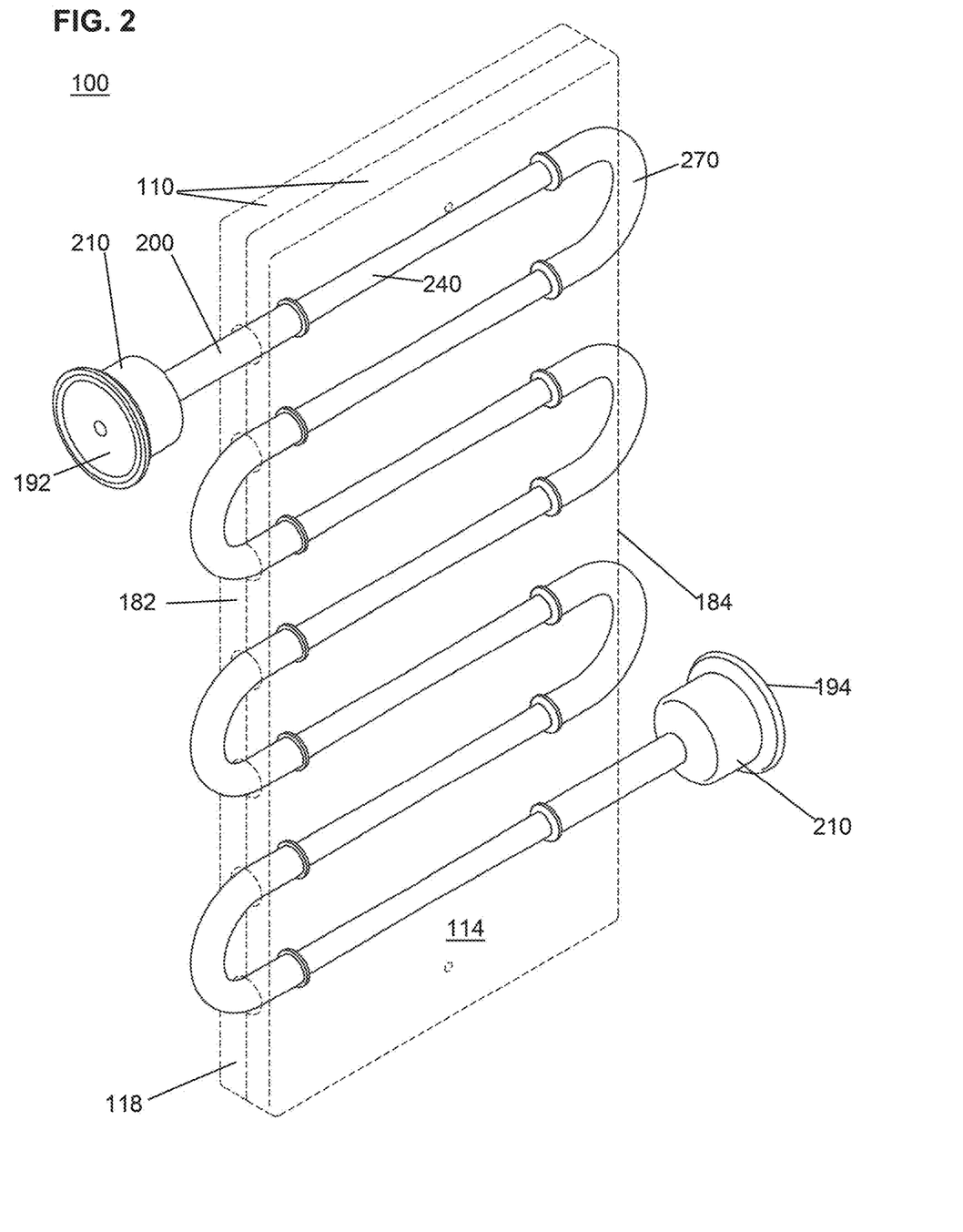
FIG. 2 shows the heat exchanger assembly 100 of FIG. 1 but without the Peltier devices 140, and without the clasps 130.

FIG. 2.

FIG. 2 shows the heat exchanger assembly 100 of FIG. 1 but without the Peltier devices 140, and without the clasps 130. The casing 110 with the first piece 114 and the second piece 118 are shown in their operational positions—abutting one another. The casing 110 has been rendered transparent so that the details of the heat exchanger tubing assembly 200 can be introduced.

Figure 3:
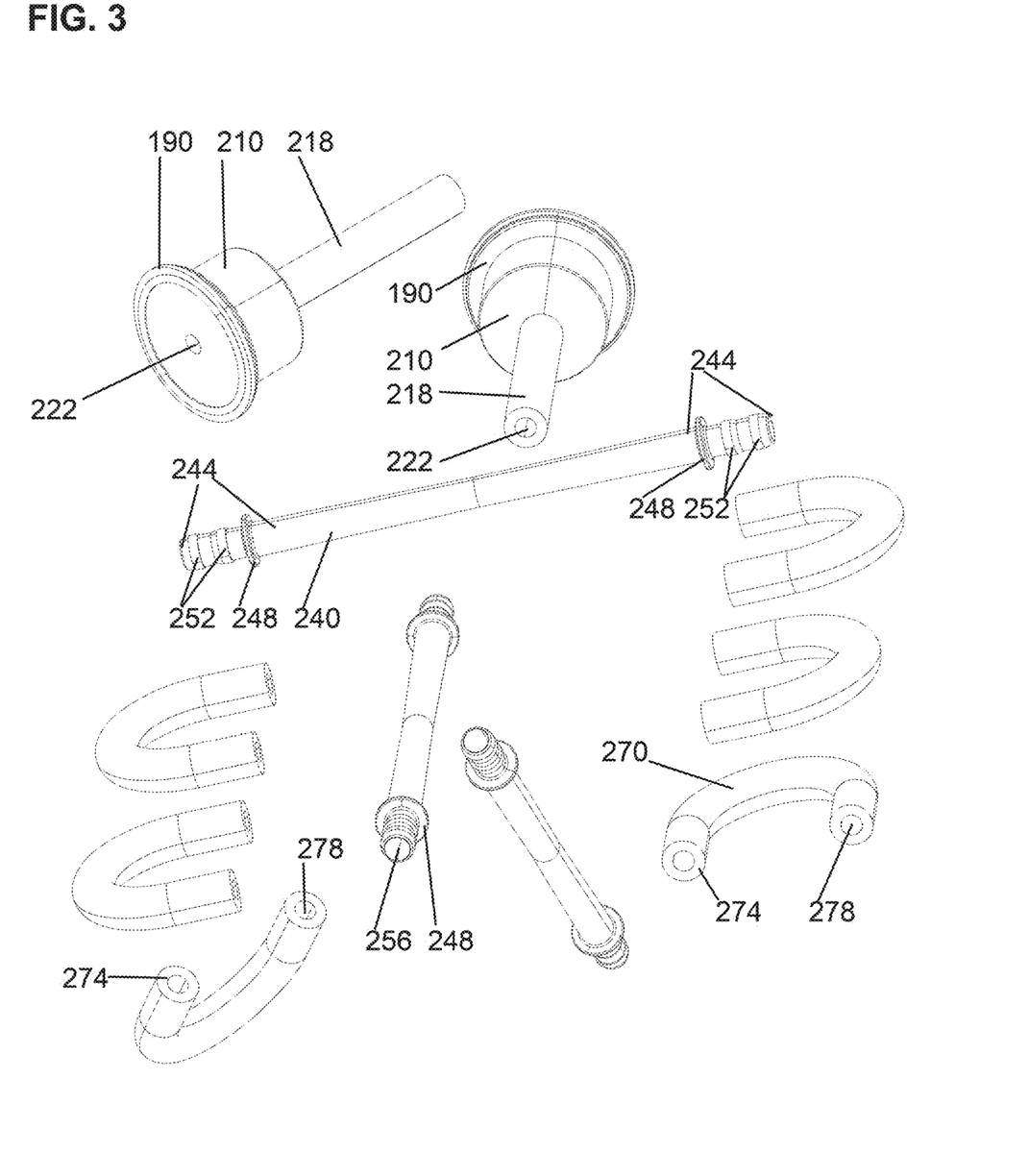
FIG. 3 shows the three components of the heat exchange tubing assembly 200.

FIG. 3.

FIG. 3 shows the three components of the heat exchange tubing assembly 200 (FIG. 2). The components are connector tubes 210, conductive segments 240, and curved connectors 270. To avoid unnecessary clutter, only three conductive segments 240 are shown. Several of the pieces have been rotated to show different views of the component.

The conductive segments 240 have two identical end portions 244 with flanges 248 and barbed portions 252. The barbed portions 252 may be inserted into appropriately sized tubing to form a sealed connection. The conductive segments 240 have a longitudinal bore 256 that allows liquid to flow through the conductive segment 240.

The two connector tubes 210 are interchangeable. Each has a sanitary fitting 190 at one end and a flexible tube 218 at the other that receives the barbed portion 252 from a conductive segment 240. A longitudinal channel 222 in each connector tube 210 allows liquid to flow through the connector tube 210.

Each of the curved connectors 270 has a pair of flexible openings 274 to receive the barbed portion 252 from a conductive segment 240. An interior channel 278 connects the flexible openings 274 to allow liquid to flow through the curved connector 270.

Returning to FIG. 2, one can see that a flow path for liquid exists from through a longitudinal channel 222 in a first connector tube 212 at a proximal end 192 of the flow path on a first side 182 of the conductive casing 110. The flow path continues into an alternating series of conductive segments 240 and curved connectors 270, ending with a final conductive segment 246 that is connected to a second connector tube 216 at a distal end of the flow path 196. In this figure the first connector tube 212 is on a first side 182 of the conductive casing 110 and the second connector tube 216 is on a second side 184 of the conductive casing 110. One of skill in the art will appreciate that both connector tubes 210 could be on a first side 182 of the conductive casing 110.

Figure 4:
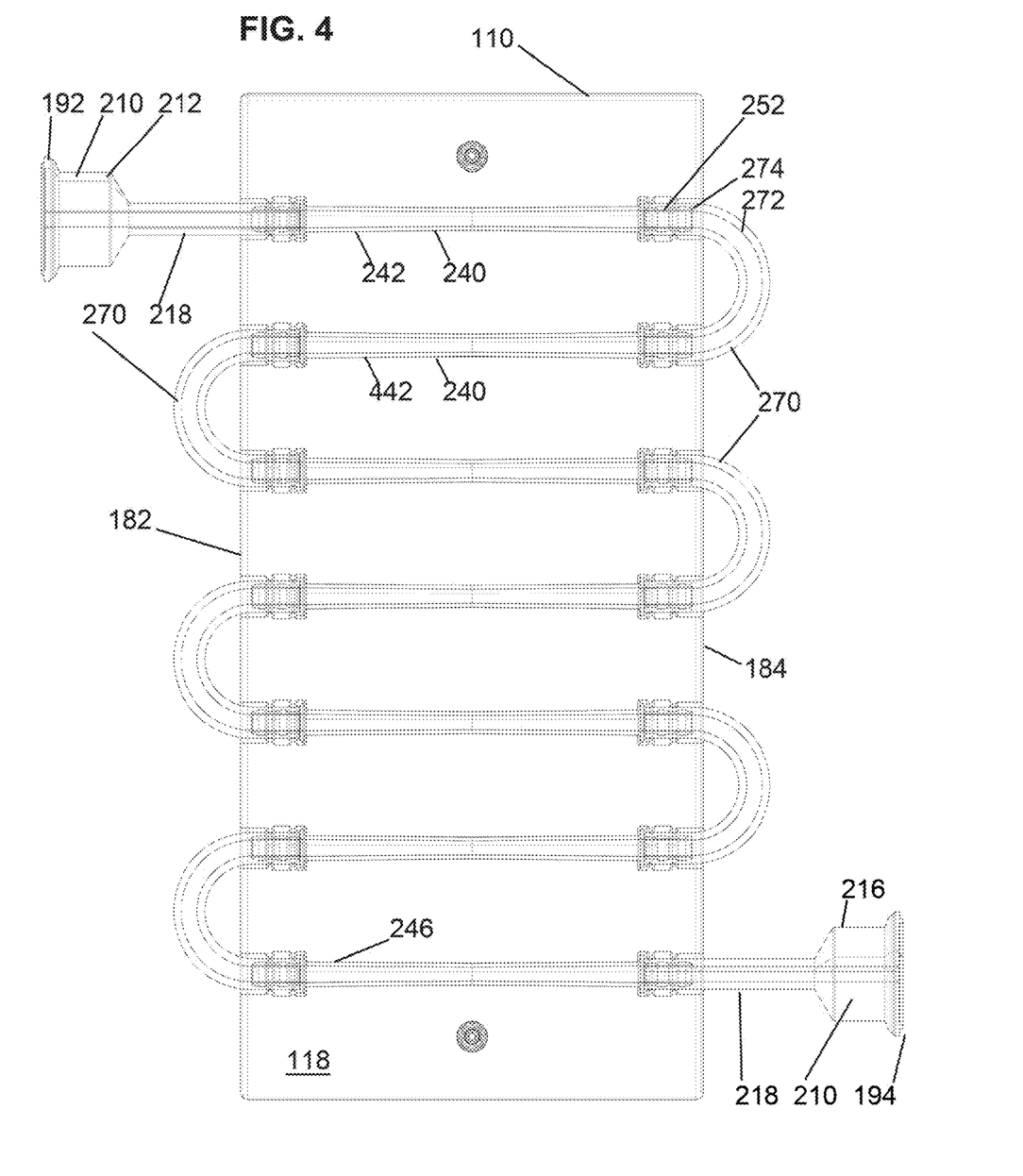
FIG. 4 provides a cross section of the heat exchange assembly 100 taken between the first piece 114 and 118 and thus bisecting the heat exchanger tubing assembly 200.

FIG. 4.

FIG. 4 provides a cross section of the heat exchange assembly 100 taken between the first piece 114 and 118 and thus bisecting the heat exchanger tubing assembly 200. The flow path from the proximal end 192 of the first connector tube 212 to the distal end 194 of the second connector tube 216 is shown in FIG. 4. Visible in FIG. 4 are the barbed connections between the barbed portions 252 of the conductive segments 240 and the flexible tubes 218 of the connector tubes 210. Also visible is the first curved connector 272 connecting the first connector tube 242 to the second connector tube 442. Also visible in FIG. 4 are the barbed connections between the barbed portions 252 of the conductive segments 240 and the flexible openings 274 of the curved connectors 270. For a barbed connection to work well, the barbs must be received into flexible tubing so that the barbs extend into the flexible tubing to seal the flow path around the perimeter of the barbed connection. The barbed portion may be rigid.

To help explain the flow path, specific instances of conductive segments 240, connector tubes 210, and curved connectors 270 have been give specific element numbers in FIG. 4. The flow of liquid through the heat exchanger tubing assembly 200 is:

- into the longitudinal channel 222 of the first connector tube 212 outside of the conductive casing 110 and then passing into the conductive casing 110;
- from the first connector tube 212 through the longitudinal bore 256 of the first conductive segment 242;
- from the first conductive segment 242 into the interior channel 278 of the first curved connector 272;
- through an alternative sequence of conductive segments 240 and curved connectors 270 into the longitudinal bore 256 of the final conductive segment 246; and
- from the final conductive segment 246 through the second connector tube 216 and out of the conductive casing (110).

After the second connector tube 216, the liquid continues into other tubing and components after being thermally conditioned in the heat exchange assembly 100.

Figure 5:
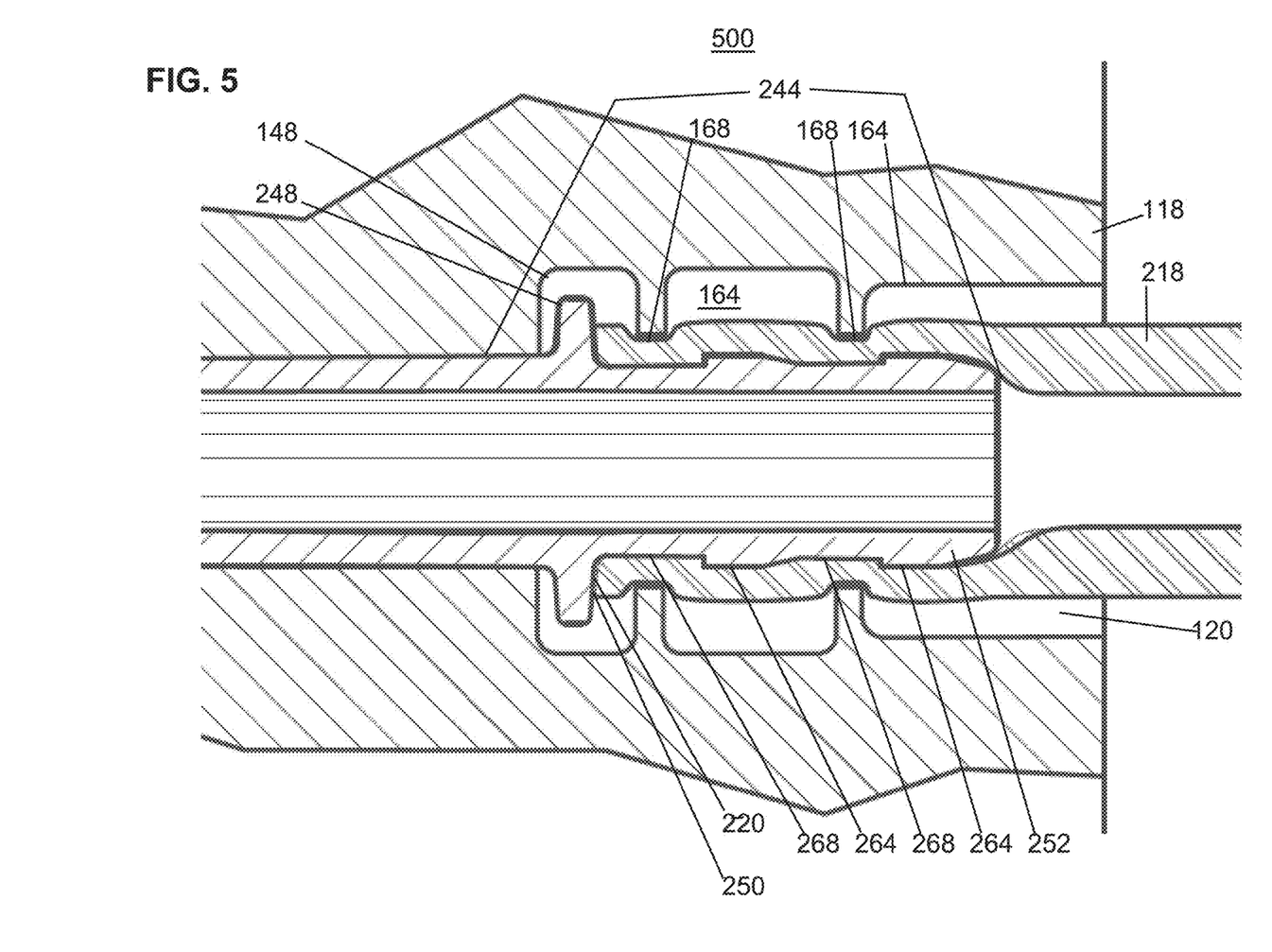
FIG. 5 is an enlarged portion of FIG. 4 that shows an enhanced barbed connection 500.

FIG. 5.

FIG. 5 is an enlarged portion of FIG. 4 that shows an enhanced barbed connection 500 in a portion of second piece 118. The end portion 244 of a conductive segment 240 is shown in engagement with the flexible tube 218 of the connector tube 210 on the distal end 194 of the flow path. The barbed portion 252 of the conductive segment 240 is shown in detail. The barbed portion has a set of two raised portions 264 that press into the inner walls of the flexible tube 218 and two non-raised gaps 268.

The conductive casing 110 as visible in second piece 118 has a series of features to interact with the end portion 244 of a conductive segment 240 and the engagement with the flexible tube 218 of the connector tube 210. More specifically, the second piece 118 has a flange retention void 148 which receives the flange 248 of the connector tube and thus helps to retain both the flanges 248 of both the first connector tube 212 and second connector tubes 216 and the curved connectors 270 in a limited position within the conductive casing 110 but by extension, helps minimize movement of the entire heat exchanger tubing assembly 200 within the conductive casing 110.

The conductive casing 110 also has a set of barb voids 164 to receive the portion of the flexible tube 218 of the connector tube 210 that have the raised portions 264 of the barbed portion 252. The conductive casing 110 has a set of compression rings 168 that compress the flexible tube 218 of the connector tube 210 in the non-raised gaps 268 of the barbed portion 252 to augment the barbed seal. The first piece 114 and the second piece 118 each having a segment of the compression ring 168. The alignment of the barb voids 164 with the raised portions 264 and the alignment of the compression rings 168 with the non-raised gaps 268 is made possible by the alignment of the flange 248 with the flange retention void 148.

Figure 6:
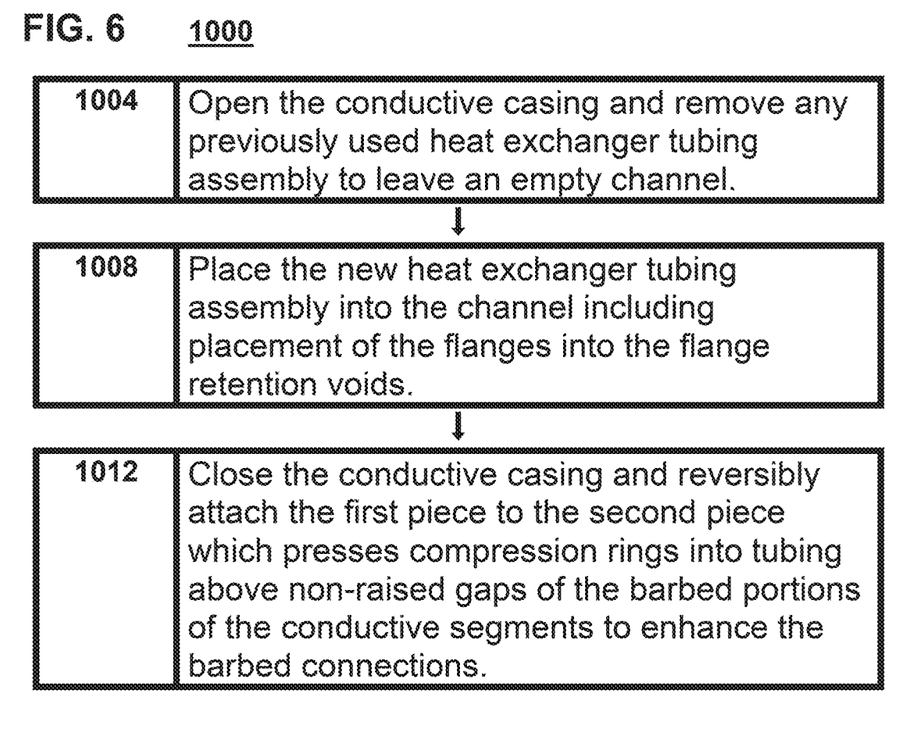
FIG. 6 is a flow chart for a process 1000 to insert a heat exchanger tubing assembly 200 in the conductive casing 110 for a heat exchanger assembly 100.

FIG. 6 is a flow chart for a process 1000 to insert a heat exchanger tubing assembly 200 in the conductive casing 110 for a heat exchanger assembly 100.

Step 1004—Open the conductive casing 110 and remove any previously used heat exchanger tubing assembly 200 to leave an empty channel 120 in the conductive casing 110.

Step 1008—Place the new heat exchanger tubing assembly 200 into the channel including placement of the flanges 248 into the flange retention voids 148.

Step 1012—Close the conductive casing 110 and reversibly attach the first piece 114 to the second piece 118 which presses compression rings 168 into flexible tubing 218, 274; above non-raised gaps 268 of the barbed portions 252 of the conductive segments 240 to form a set of enhanced barbed connections 500.

Preferred Materials.

Conductive Segments.

The conductive segments 240 need to be made of a biocompatible material that has high thermal conductivity in the radial direction. This high thermal conductivity will allow heat to flow from the conductive casing 110 to the liquid in the conductive segments 240 for heating processes or conversely the high thermal conductivity will allow heat to flow to the conductive casing 110 from the liquid in the conductive segments 240 for cooling processes. A higher thermal conductivity means that the number of conductive segments 240 for a particular change in temperature can be reduced relative to what would be needed with conductive segments made of a material with a lower thermal conductivity.

A suitable material is Trilliant™ Nylon 6 available from AVIENT of Avon Lake, Ohio (www.Avient.Com (spaces added to avoid a live link). Nylon 6 is also known as polycaprolactam or polyamide 6 and is a well-known material. Nylon 6 may be used in injection molding equipment. For context, the conductive segments 240 shown in the figures of this application are approximately seven inches long.

The standard unit of measurement for thermal conductivity is watts per meter-kelvin. Detailed testing of thermal conductivity will look at the thermal conductivity in a plane of the material and also through plane which is perpendicular to the plane of the material. For this application, the through plane value is the most relevant. The tested through plane thermal conductivity of a batch of Trilliant™ Nylon 6 using ASTM E1461 testing protocol was 0.79 W/mK. While this level of thermal conductivity is much less than copper and other thermal conductors, it is much better than most thermal insulators.

For comparison, the thermal conductivity values for various substances are set forth below.

| Material | Thermal Conductivity in W/mK |
| --- | --- |
| Air | 0.026 |
| Styrofoam | 0.033 |

| Material | Thermal Conductivity in W/mK |
|---|---|
| Polyamide (Nylon) | 0.25 |
| Water (as 20° C.) | 0.6 |
| Copper | 384.1 |

A paper by a NanoEngineering Group at MIT notes that "bulk polymers usually have low thermal conductivity, ~0.1-0.3 Wm-1K-1, due to the presence of defects such as polymer chain ends, entanglement, random orientation, voids and impurities, etc." See Polymers with Hight Thermal Conductivity at https://web.mit.edu/nanoengineering/research/polymers.shtml #(spaces added to avoid live link)

The thermal conductivity of unfilled polymers is generally low making them insulators with thermal conductivity in the range of 0.1 to 0.5 W/mK. The thermal conductivity can be boosted by adding thermally conductive fillers to the polymer material to make a filled polymer. Depending on the type of filler and the concentration of the filler, this can move the thermal conductivity to above 1 W/mK and possibly much higher than that.

One of skill in the art will appreciate that Trilliant™ Nylon 6 is polymer with fillers to enhance the thermal conductivity beyond the base value which would likely be about 0.25 W/mK. Those of skill in the art could substitute other filled polymers with thermal conductivity of equal or exceeding Trilliant™ Nylon 6. Materials with a thermal conductivity slightly below Trilliant™ Nylon 6 could be used but one would prefer a material with thermal conductivity that is greater than the thermal conductivity of water, that is 0.6 W/m K.

Conductive segments could be made from metal such as aluminum, stainless steel, or other materials keeping in mind the needs for biocompatibility and the need to create the flange 248 and barbed portion 252. The added costs for making these conductive segments would be partially offset by decreasing the overall size of the heat exchanger assembly 100 as higher thermal conductivity would allow for a shorter run length of the path within the conductive casing 110. If metallic conductive segments could be sterilized and used again, then the economics of using the metallic conductive segments would be less of a barrier.

Connector Tubes and Curved Connectors

The barbed connections between the barbed portions 252 of the conductive segments 240 and the flexible tubes 218 of the connector tubes 210 requires a material that will deform to allow the barbed portions 252 to seal the flow path and avoid leaks. The same is true for the barbed connection between the barbed portions 252 of the conductive segments 240 and the flexible openings 274 of the curved connectors 270. So while it is not required that the flexible tubes 218 be made of the same material as the curved connectors 270, the physical properties will be similar. In both cases, a biocompatible tubing material is needed. An example of suitable tubing material is Tufel™ III two component silicone rubber material sold by Momentive™ (www.momentive.com Spaces added to avoid live link). This is a platinum cured silicon. These materials come in a variety of durometer values so that a designer can make an appropriate choice. Those of skill in the art could find another polymer that has suitable biocompatibility and mechanical properties.

Clean Views.

It can be useful to include a set of clean views of the heat exchanger tubing assembly 200 without the distraction of many lead lines and many element numbers. A set of clean views is provided.

Figure 7:
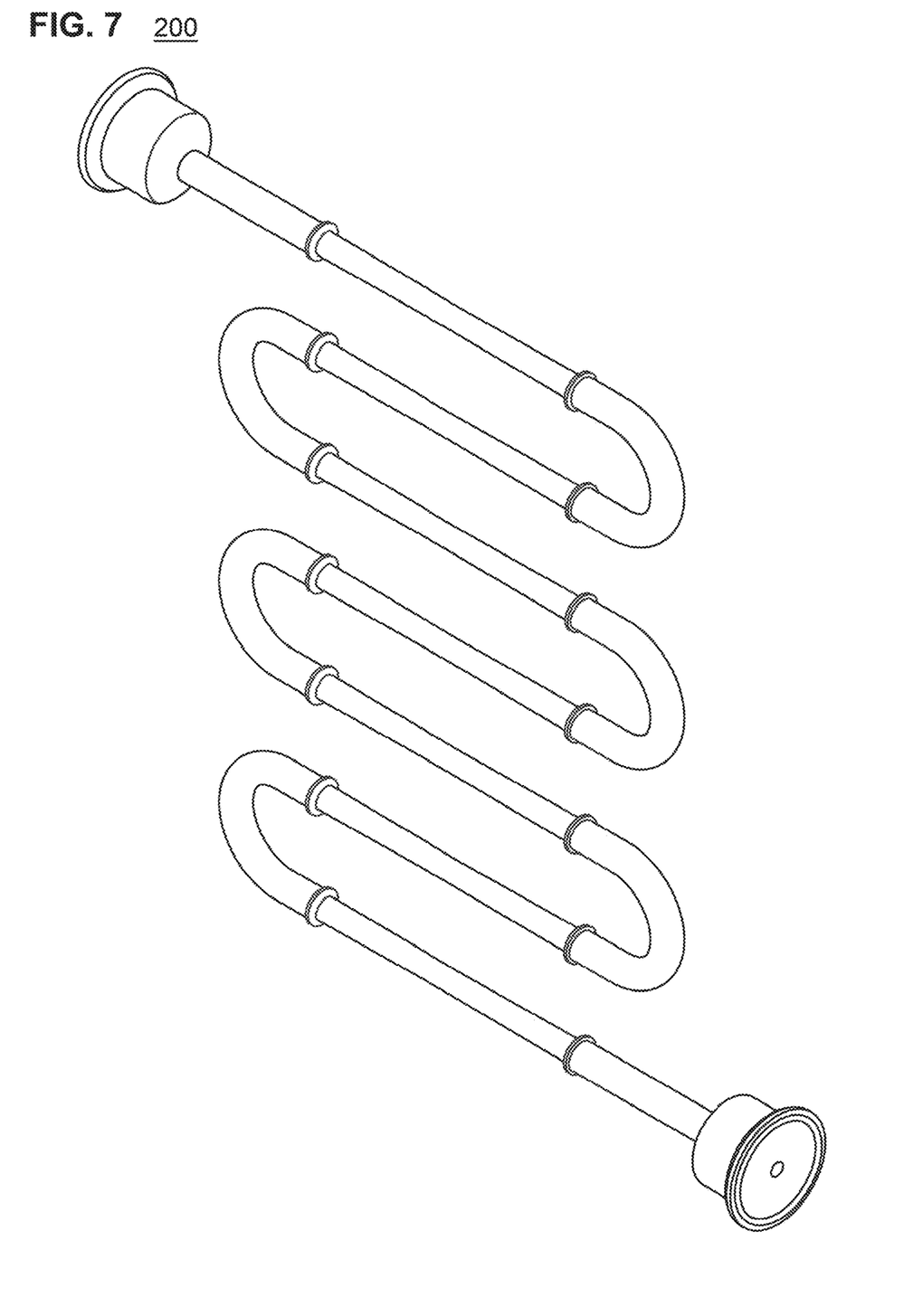
FIG. 7 is a top, front, left side perspective view of heat exchanger tubing assembly 200.

FIG. 7 is a top, front, left side perspective view of heat exchanger tubing assembly 200.

Figure 8:
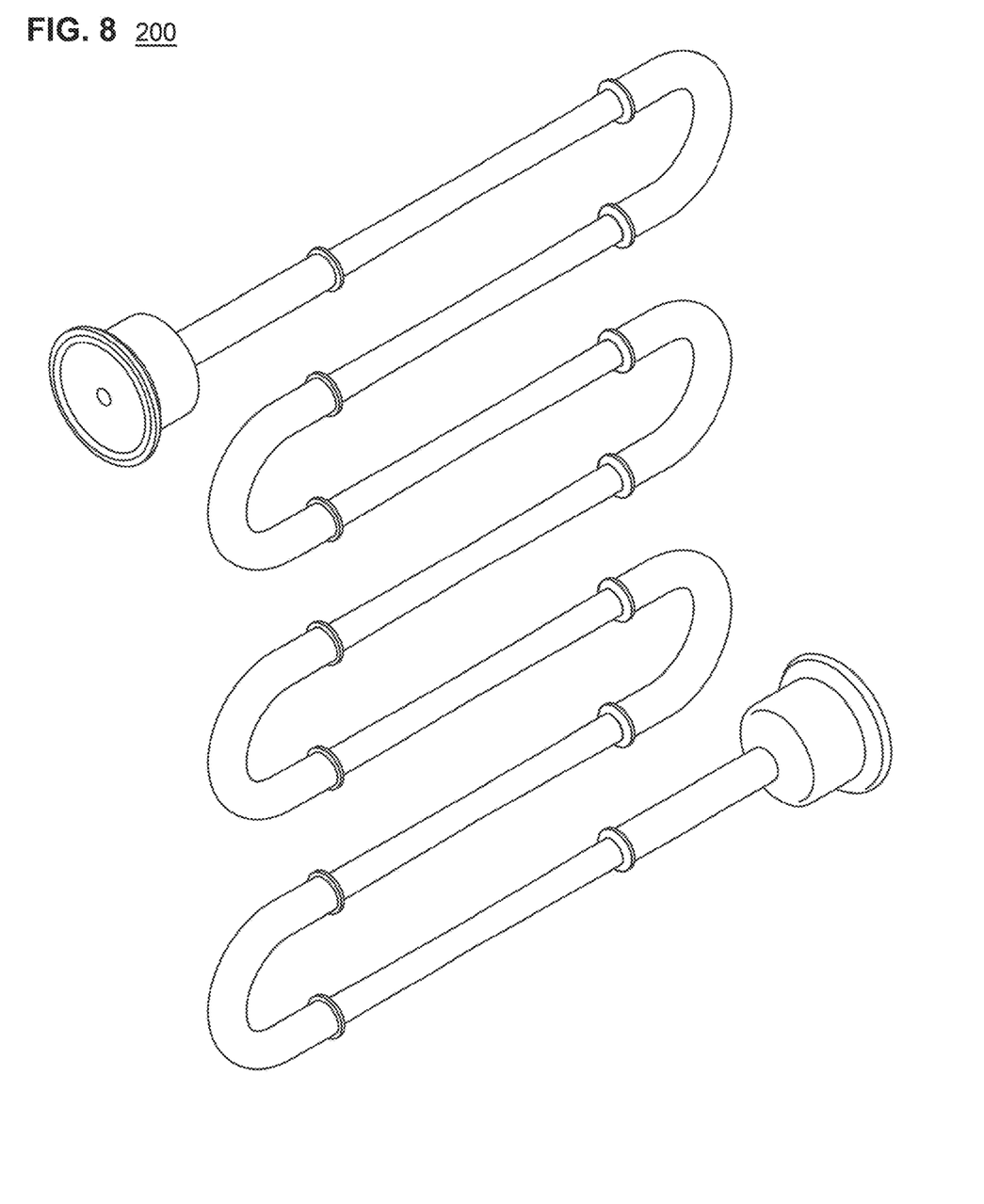
FIG. 8 is a top, front, right side perspective view of heat exchanger tubing assembly 200.

FIG. 8 is a top, front, right side perspective view of heat exchanger tubing assembly 200.

Figures 9, 12, 13:
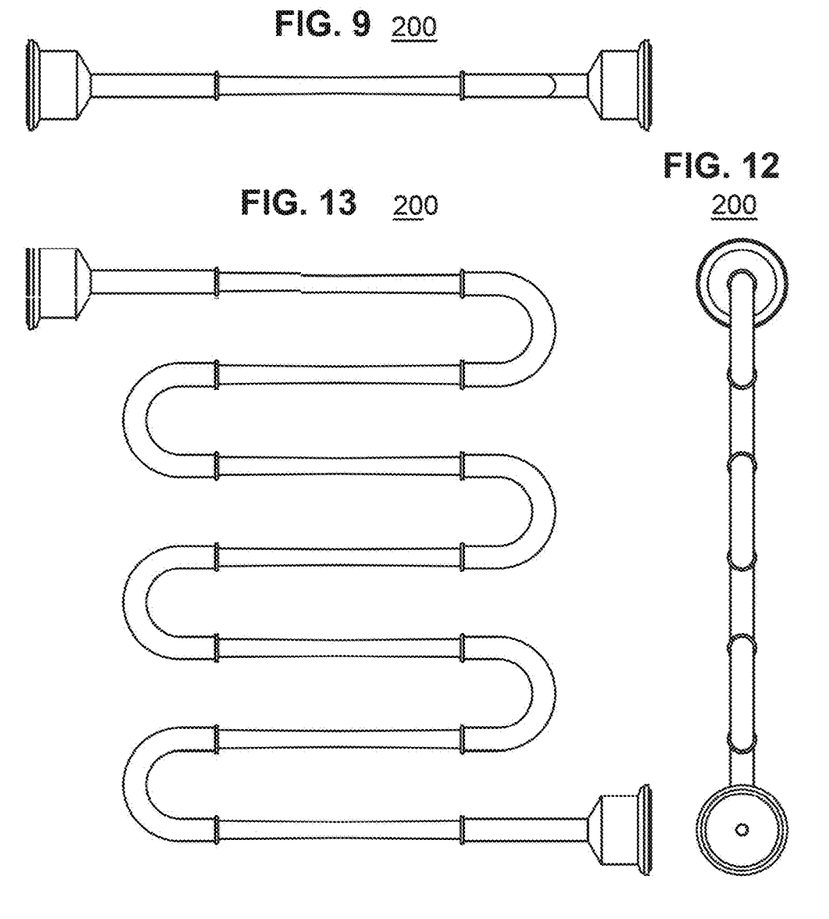
FIG. 9 is a front elevation view of heat exchanger tubing assembly 200.
FIG. 12 is a left elevation of heat exchanger tubing assembly 200.
FIG. 13 is a top plan view of heat exchanger tubing assembly 200.

FIG. 9 is a front elevation view of heat exchanger tubing assembly 200.

Figure 10:
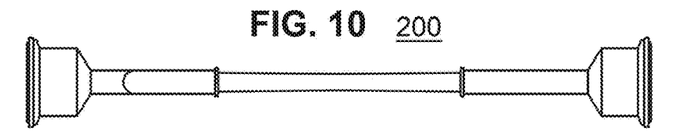
FIG. 10 is a rear elevation view of heat exchanger tubing assembly 200.

FIG. 10 is a rear elevation view of heat exchanger tubing assembly 200.

Figure 11:
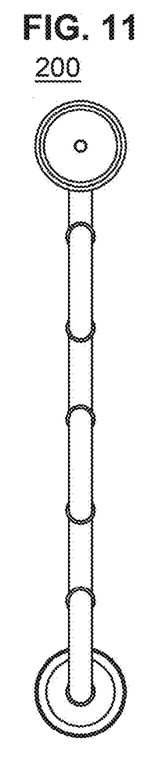
FIG. 11 is a right elevation view of heat exchanger tubing assembly 200.

FIG. 11 is a right elevation view of heat exchanger tubing assembly 200.

FIG. 12 is a left elevation of heat exchanger tubing assembly 200.

FIG. 13 is a top plan view of heat exchanger tubing assembly 200.

Figure 14:
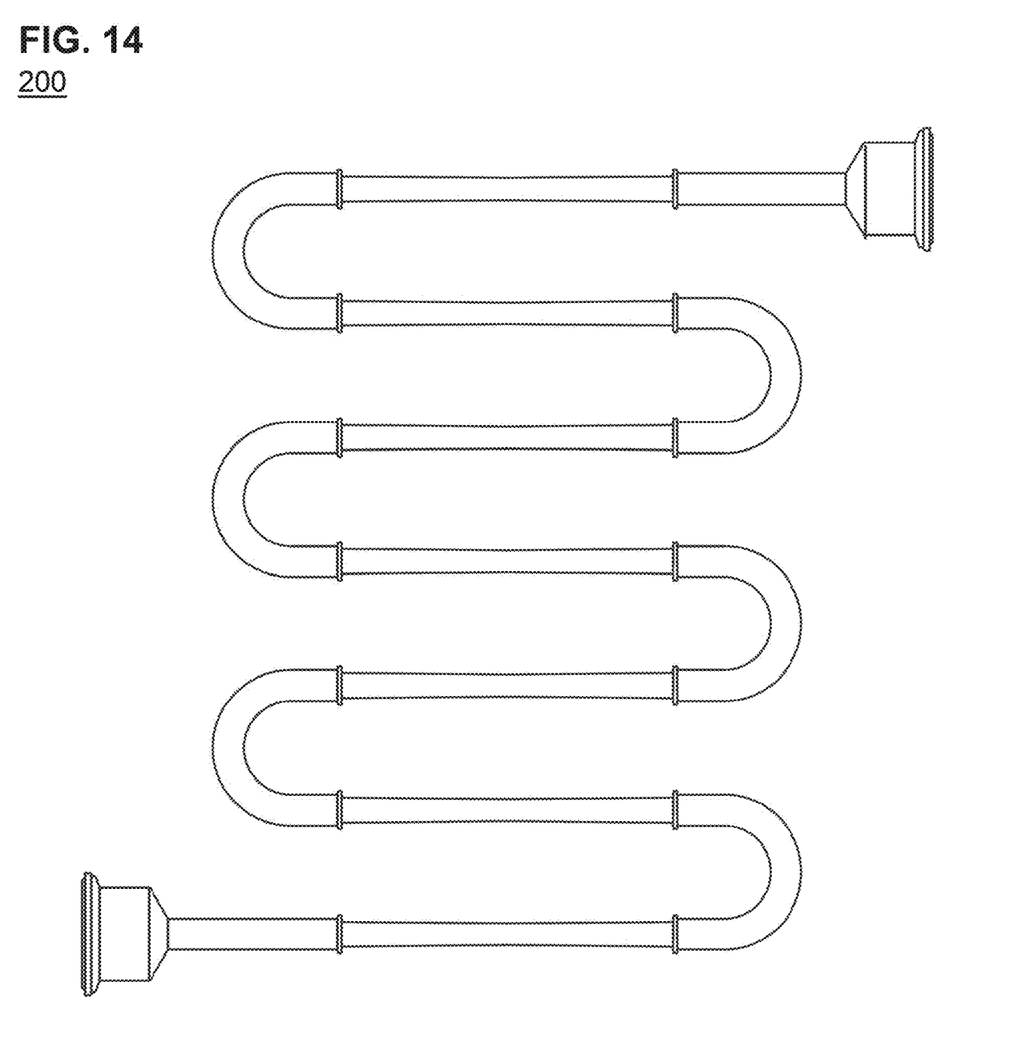
FIG. 14 is a bottom plan view of heat exchanger tubing assembly 200.

FIG. 14 is a bottom plan view of heat exchanger tubing assembly 200.

Figure 15:
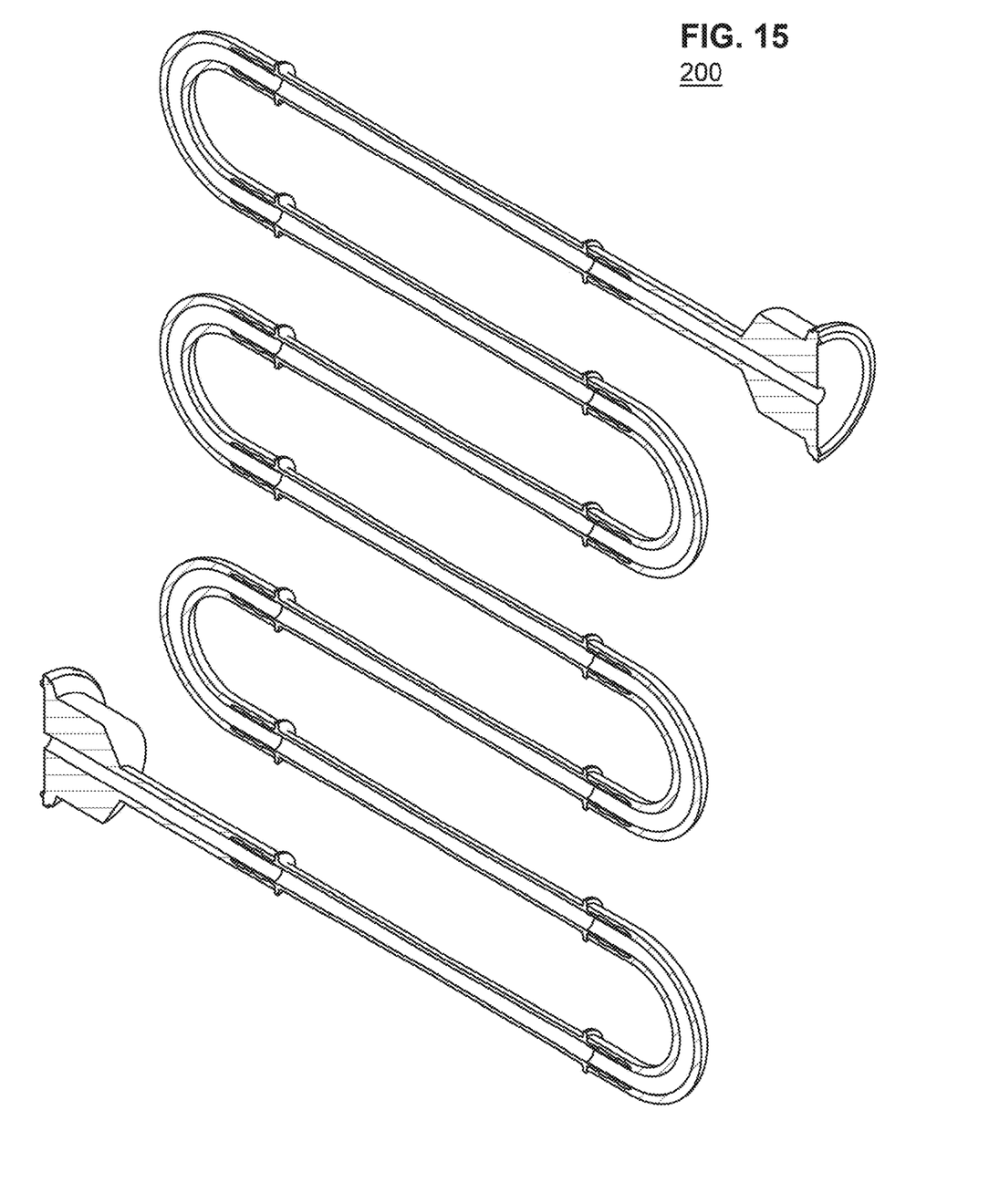
FIG. 15 is a cross section of a bottom, front, right perspective view of heat exchanger tubing assembly 200.

FIG. 15 is a cross section of a bottom, front, right perspective view of heat exchanger tubing assembly 200.

Alternatives and Variations

Flange Placement.

Returning to FIG. 5, the figures in this disclosure showed conductive segments 240 with flanges 248 located at the edge of the barbed portions 252. This positioning works well as the leading edge 220 of the tubing that engages with the barbed portions 252 can abut the flange 248 so that the flange 248 serves as a stop face 250 that stops the relative movement of the leading edge of the flexible tubing. Other designs are possible with a stop face to abut the leading edge of the tubing and a radially larger flange to engage the flange retention void 148 set back from the barbed portion 252. This would require a corresponding change in the placement of the flange retention void 148 in the conductive casing 110.

Connector Tube.

The connector tubes 210 have been shown with sanitary fittings which may be used in clamps that are designed for use with sanitary fittings. See for example, U.S. Pat. No. 11,629,804 for Asymmetric Clamp for Joining Sanitary Fittings. But the connector tubes 210 could be a straight tube without a fitting on either end. Such tubes could engage with a barbed connector or other connection types known in the art.

Location of the Curved Connectors.

The figures in this disclosure have shown the curved connectors 270 with a pair of flexible openings 274 engaged with the barbed portions 252 of the conductive segments 240 within the conductive casing 110 but with at least a portion of the curved connectors 270 located outside of the conductive casing 110. This is a good choice as the curved connectors 270 are made of a material with low thermal conductivity and the curved connectors 270 thus insulate the heat treated liquid while outside of the conductive casing 110.

Those of skill in the art will appreciate that the conductive casing could be enlarged and the flexible tubes 218 of the connector tubes 210 extended so that the curved connectors 270 are located entirely within the conductive casing 110 so that only the two connector tubes 210 extend outside of the conductive casing 110.

End Use of the Heat-Treated Liquid.

In many instances the liquid which is heated or cooled using the teachings of the present disclosure will be in a process that has a modified liquid as an end product such as in the production of pharmaceuticals or liquids relevant to the production of pharmaceuticals. However, the present disclosure does not rely on the end use of the liquid. The liquid that is heated or cooled could be used on a closed loop system to alter the temperature of some other liquid or solid item through heat transfer through a set of tubing that holds the liquid when not in the heat exchanger assembly 100. The liquid could be the water or salt water for an aquarium. The use of the liquid does not matter.

One of skill in the art will recognize that some of the alternative implementations set forth above are not universally mutually exclusive and that in some cases additional implementations can be created that employ aspects of two or more of the variations described above. Likewise, the present disclosure is not limited to the specific examples or particular embodiments provided to promote understanding of the various teachings of the present disclosure. Moreover, the scope of the claims which follow covers the range of variations, modifications, and substitutes for the components described herein as would be known to those of skill in the art.

Where methods and/or events described above indicate certain events and/or procedures occurring in a certain order, the ordering of certain events and/or procedures may be modified. Additionally, certain events and/or procedures may be performed concurrently in a parallel process when possible, as well as performed sequentially as described above.

The legal limitations of the scope of the claimed invention are set forth in the claims that follow and extend to cover their legal equivalents. Those unfamiliar with the legal tests for equivalency should consult a person registered to practice before the patent authority which granted this patent such as the United States Patent and Trademark Office or its counterpart.

What is claimed is:

1. A heat exchanger tubing assembly (200) for insertion into a channel (120) in a conductive casing (110) having a first piece (114) and a second piece (118), so that thermal treatment applied to the conductive casing may be transferred through the heat exchanger tubing assembly to a liquid passing through the heat exchanger tubing assembly to create a heat-treated liquid, the heat exchanger tubing assembly comprising:
   a set of at least two conductive segments (240) comprising a first conductive segment (242) and a second conductive segment; each conductive segment made of a first material of first thermal conductivity value, each conductive segment short enough to fit into the channel in the conductive casing so that neither a first end portion (244) nor a second end portion (244) of the conductive segment extends out of the conductive casing;
   both the first end portion and the second end portion of each conductive segment (240) having a barbed portion (252) and a flange (248) that extends radially outward from the conductive segment;
   each conductive segment having a longitudinal bore (256) to allow liquid to pass through the conductive segment;
   a first connector tube (212) with a flexible tube (218) connected to the first end portion of the first conductive segment (242) to allow liquid to enter a proximal end (192) of the first connector tube (212) outside of the conductive casing and travel through a longitudinal channel (222) then out a distal end of the first connector tube into the longitudinal bore (256) of the first conductive segment (242);
   the flexible tube (218) made of a second material with a second thermal conductivity value which is lower than the first thermal conductivity value;
   a first curved connector (272) with an interior channel (278), the first curved connector made of a third material with a third thermal conductivity value which is lower than the first thermal conductivity value;
   the first curved connector connecting the second end portion of the first conductive segment and a first end portion of the second conductive segment (442);
   a second connector tube (210) with flexible tube (218), connected to a distal end of a final conductive segment to allow liquid to enter a proximal end of the second connector tube inside of the conductive casing and travel out a distal end of the second connector tube outside of the conductive casing into a subsequent flow path for the heat-treated liquid; and
   wherein the set of flanges extending radially outward may be used to engage with flange receiving voids in the conductive casing to help position the heat exchanger tubing assembly within the conductive casing.

2. The heat exchanger tubing assembly of claim 1 wherein the second conductive segment is the final conductive segment so that a flow path for the liquid passing through the conductive casing (110) is:
   into the first connector tube (210) outside of the conductive casing (110);
   from the first connector tube through the longitudinal bore (256) of the first conductive segment (240);
   from the first conductive segment into the interior channel (278) of the first curved connector (270);
   from the first curved connector into the longitudinal bore (256) of the final conductive segment (240); and
   from the final conductive segment through the second connector tube (210) and out of the conductive casing (110).

3. The heat exchanger tubing assembly of claim 1 wherein the second conductive segment is not the final conductive segment so that a flow path for the liquid passing through the conductive casing includes passage through:
   the longitudinal channel (222) of the first connector tube (210) and passing into the conductive casing;
   through a series of at least three conductive segments which are joined by curved connectors; and
   through the final conductive segment (246) of the series of at least three conductive segments then into the second connector tube (216) and out of the 9 conductive casing (110).

4. The heat exchanger tubing assembly of claim 1 wherein the first connector tube (212) enters a first side (182) of the conductive casing and the second connector tube (216) exits the first side (182) of the conductive casing.

5. The heat exchanger tubing assembly of claim 1 wherein the first connector tube (212) enters a first side (182) of the conductive casing and the second connector tube (216) exits a second side (184) of the conductive casing which is different from the first side.

6. The heat exchanger tubing assembly of claim 1 wherein at least one curved connector is entirely contained in the channel in the conductive casing so that none of the curved connector is exposed to ambient air that surrounds the conductive casing.

7. The heat exchanger tubing assembly of claim 1 wherein at least one curved connector is not entirely contained in the channel in the conductive casing so that at least some of curved connector is exposed to ambient air that surrounds the conductive casing.

8. The heat exchanger tubing assembly of claim 1 wherein the proximal end (192) of the first connector tube (212) has a sanitary fitting (190) for use in a sanitary fitting clamp.

9. The heat exchanger tubing assembly of claim 1 wherein the proximal end (192) of the first connector tube (212) ends without a fitting so that other tubing with a terminal fitting may connect with the proximal end of the first connector tube.

10. The heat exchanger tubing assembly of claim 1 wherein the second thermal conductivity value equals the third thermal conductivity value.

11. The heat exchanger tubing assembly of claim 1 wherein the second thermal conductivity value is different from the third thermal conductivity value.

12. The heat exchanger tubing assembly of claim 1 wherein the conductive segments are formed using a polymer with fillers to enhance the first thermal conductivity value.

13. The heat exchanger tubing assembly of claim 1 wherein the conductive segments are formed using Nylon 6 with fillers to enhance the first thermal conductivity value.

14. The heat exchanger tubing assembly of claim 1 wherein the conductive segments are formed of a conductive material with a through plane thermal conductivity of not less than 0.79 W/m K.

15. The heat exchanger tubing assembly of claim 1 wherein the conductive segments are formed of a conductive material with a through plane thermal conductivity of not less than 0.6 W/m K.

16. The heat exchanger tubing assembly of claim 1 wherein the conductive segments are formed of metal.

17. A process to insert a new heat exchanger tubing assembly (200) of claim 1 into a conductive casing (110);

opening the conductive casing (110) and removing any previously used heat exchanger tubing assembly (200) to empty a channel (120) in the conductive casing (110);

placing the new heat exchanger tubing assembly (200) into the channel (120) including placement of flanges (248) into flange retention voids (148); and closing the conductive casing (110) and reversibly attach a first piece (114) to a second piece (118) which presses compression rings (168) into flexible tubing (218, 274) above non-raised gaps (268) of barbed portions (252) of conductive segments (240) to form a set of enhanced barbed connections (500).

18. The process of claim 17 wherein the new heat exchanger tubing assembly (200) includes curved connectors (270) that join pairs of conductive segments (240) and the channel (120) within the conductive casing (110) receives the curved connectors (270) so that no part of a curved connector (270) extends out of the casing (110).

19. The process of claim 17 wherein the new heat exchanger tubing assembly (200) includes curved connectors (270) that join pairs of conductive segments (240) and the channel (120) within the conductive casing (110) receives only a portion of each of the curved connectors (270) so that each of the curved connector (270) extends out of the casing (110).

* * * * *

UNITED STATES PATENT AND TRADEMARK OFFICE
CERTIFICATE OF CORRECTION

| | | |
|---|---|---|
| PATENT NO. | : 12,339,074 B1 | Page 1 of 1 |
| APPLICATION NO. | : 19/044179 | |
| DATED | : June 24, 2025 | |
| INVENTOR(S) | : Morano, III et al. | |

It is certified that error appears in the above-identified patent and that said Letters Patent is hereby corrected as shown below:

In the Claims

Column 12, Line 47, Claim 3 'the 9 conductive casing' should read -the conductive casing-.

Signed and Sealed this
Nineteenth Day of August, 2025

Coke Morgan Stewart
*Acting Director of the United States Patent and Trademark Office*